United States Patent [19]

Audeh et al.

[11] Patent Number: 5,461,180

[45] Date of Patent: Oct. 24, 1995

[54] CATALYTIC NORBORNYLATION OF AROMATICS

[75] Inventors: Costandi A. Audeh, Princton, N.J.; James R. Boulton, Chalfont, Pa.; Ross A. Kremer, Ringoes, N.J.; Yusheng Xiong, Newtown, Pa.

[73] Assignee: Mobil Oil Corporation, Fairfax, Va.

[21] Appl. No.: 239,189

[22] Filed: May 5, 1994

[51] Int. Cl.$^6$ ..................... C07C 2/66
[52] U.S. Cl. ............. 585/467; 585/446; 585/452
[58] Field of Search .................. 585/24, 25, 26, 585/375, 376, 446, 452, 467

[56] References Cited

FOREIGN PATENT DOCUMENTS 0504541  9/1992  European Pat. Off. .

OTHER PUBLICATIONS

Larock, R. C. and Johnson, P. L., J. Chem. Soc. Chem. Commun., 1368 (1989).

Brown, H. C. et al., JACS 97:3,610 (1975).

*Primary Examiner*—P. Achutamurthy
*Attorney, Agent, or Firm*—Alexander J. McKillop; Dennis P. Santini; Robert B. Furr, Jr.

[57] ABSTRACT

A process is disclosed for the catalytic norbornylation of aromatics comprising the steps of contacting norborene and an aromatic hydrocarbon with a solid catalyst comprising a porous crystalline material having a Constraint Index of from about 0.1 to about 12 under norbornylation conditions to evolve a product containing norbornylated aromatics.

10 Claims, No Drawings

CATALYTIC NORBORNYLATION OF AROMATICS

FIELD OF THE INVENTION

This invention relates a method for making norbornylated aromatics which are useful as high density fuels. The invention further provides a high density fuel comprising norbornylated aromatics.

BACKGROUND OF THE INVENTION

Norbornylation of aromatics via complex techniques is described in the literature, but the literature also discloses that no direct, simple, and potentially low-cost methods are known. Larock et al. disclose a 43–74% yield of a mixture of exo-2-phenylnorbornane and the double insertion product (phenylated norbornene dimer) by reaction of norbornene with iodobenzene using a complex homogeneous catalyst system consisting of $Pd(OAc)_2$, $n\text{-}Bu_4NCl$, and formate salts such as $KO_2CH$. Larock, R.C., and Johnson, P.L., *J. Chem Soc. Chem.Commun.*, 1638 (1989).

Brown, H.C. et al. describe preparation of exo-2-phenylnorbornane in 63.5% yield by norbornylation of benzene in excess benzene solvent, using large volumes of concentrated 2O sulfuric acid as the catalyst (weight ratio of concentrated $H_2SO_4$/norbornene of 2.2/1.0, mole ratio of $H_2SO_4$/norbornene of 2.7/1.0).

SUMMARY OF THE INVENTION

This invention comprises a method for the catalytic norbornylation of aromatics which comprises contacting norbornene with at least one aromatic hydrocarbon in the presence of a heterogeneous catalyst comprising a synthetic crystalline material having a Constraint Index of from about 0.1 to about 12, under catalytic norborylation conditions to produce norborylated aromatics. The method of this invention preferentially produces mono- and di-norborylated aromatics. In one embodiment, this invention provides a method for selectively converting mixtures of norbornene and aromatics to mono- and di-norbornylated aromatics in preference to the norbornene oligomers (e.g. dimers and trimers).

Aromatic feedstocks useful in the present invention include the alkyl-substituted aromatics. Both monocyclic and polycyclic aromatics are useful feedstocks. The aromatic feedstock preferably contains two or more unsubstituted ring carbon atoms, more preferably three or more unsubstituted ring carbon atoms. Examples of useful aromatic feedstocks include benzene, naphthalene, tetralin, diphenyl oxides, diphenyl sulfides, and diphenyl alkanes such as diphenyl methane as well as the corresponding mono- or di-alkyl substituted derivatives of benzene, naphthalene, tetralin, diphenyl oxides, diphenyl sulfides, and diphyenyl alkanes. If the aromatic feedstock is alkyl-substituted, the alkyl substituents typically contain from about 1 to about 30 carbon atoms, preferably from about 1 to about 20 carbon atoms. Monoalkylated aromatics having from about 8 to about 16 carbon atoms in the alkyl substituent are particularly preferred for producing synthetic lubricants while unsubstituted or short-chain alkylated aromatics are preferred for producing high density fuels. Detergent aromatics such as $C_{12}$-alkylated benzene are particularly preferred for producing a synthetic lubricant base stock, while short-chain substituted aromatics are preferred for producing a high density fuel. Nalkylene 600 brand detergent alkylated benzene (commercially available from Vista Chemical of Houston, Texas) is one example of such preferred feedstocks.

To preferentially produce mono- and di-norbornylated aromatics in accordance with the invention, the aromatics-:norbornene molar ratio in the feed is preferably at least about 2:1, more preferably from about 2:1 to about 6:1. In the embodiment which preferentially produces mono- and di-norbornylated aromatics, the norbornene oligomers (e.g. dimers and trimers) typically comprise less than about 15 weight percent of the product, preferably less than about 10 weight percent of the product.

The crystalline materials useful as catalyst components in the present process have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 0.1 and about 12. Examples of such zeolite catalysts include ZSM-4, ZSM-5, ZSM-11, ZSM12, ZSM-22, ZSM-23, ZSM-35, ZSM-48, as well as MCM-22, PSH-3, SSZ-25, and zeolite Beta.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference. Zeolite Beta is taught by U.S. Pat. Nos. 4,696,732, 3,308,069, 5,275,719, 5,258,114, and Re. 28,341, the disclosures of which are incorporated herein by reference.

Gallium-containing catalysts may be used in the present invention and are disclosed in U.S. Pat. No. 4,350,835 and U.S. Pat. No. 4,686,312, both of which are incorporated by reference as if set forth at length herein.

Zinc-containing catalysts may be used in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

Synthetic porous crystalline materials useful in the present invention also include the PSH-3 composition of U.S. Pat. 4,439,409, the SSZ-25 composition of U.S. Pat. Nos. 4,665,110 and 4,826,667, and the MCM-22 composition of U.S. Pat. 4,954,325. MCM-22 is also described in U.S. Pat. Nos. 4,992,615, 5,012,033, and 5,073,665.

The synthetic porous crystalline material, or zeolite, catalyst preferred for use in the process of this invention, referred to herein as "zeolite MCM-22" or simply "MCM-22", appears to be related to the composition named "PSH-3" described in U.S. Pat. No. 4,439,409. Zeolite MCM-22 does not appear to contain all the components apparently present in the PSH-3 compositions and is not contaminated with other crystal structures such as ZSM-12 or ZSM-5. Moreover, zeolite MCM-22 exhibits unusual sorption capacities and unique catalytic utility when compared to the PSH-3 compositions synthesized in accordance with U.S. Pat. No. 4,439,409.

Process conditions useful in the present invention are shown below. The useful process conditions do not appear to be highly feedstock-sensitive. Accordingly, the optimum process conditions (within the ranges disclosed below) for particular feedstocks may be readily determined by one of ordinary skill in the art with a minimum of trial and error.

| Catalytic Norbornylation Conversion Conditions | | | |
|---|---|---|---|
| | Useful | Typical | Preferred |
| Temperature, °C. | 75 to 300 | 100 to 300 | 125 to 275 |
| Pressure | 0 to 1000 | 0 to 750 | 0 to 500 |
| WHSV, hr.$^{-1}$ | 0.05 to 10 | 0.05 to 5 | 0.1 to 3 |

EXAMPLES

Example 1 - Preparation of Norbornylated Benzene 200 gms of benzene and 90 gms of norbornene (molar ratio of benzene/norbornene of 2.6/1) were charged to an agitated 500 cc stainless steel autoclave together with 2.3 gms of MCM-22 zeolite extrudate catalyst. The reactor was then blanketed with nitrogen, heated to 260° C., and the reaction allowed to proceed at 260° C. for six hours, at which time the norbornene was completely reacted. The reactor was then cooled to room temperature, the contents transferred to a distillation system, and the unreacted excess benzene removed by distillation. Analysis of the stripped product by GC/Mass Spec showed it to consist of 90 wt % mono-norbornylated benzene (phenyl norbornane) and 10 wt % di-norbornylated benzenes. The product was a low-viscosity liquid at room temperature having a specific gravity (15.6° C.) of 1.009, a pour point of <−57° C. and a net heat of combustion of 146,948 BTU/gallon.

Example 2 - Preparation of Norbornylated Tetralin (1,2,3,4-Tetrahydro-Naphthalene)

264 gms of tetralin (1,2,3,4-tetrahydronaphthalene) and 94 gms norbornene (mole ratio of tetralin/norbornene=2/1) were charged to an agitated 500 cc stainless steel autoclave together with 2.4 gms of MCM-22 zeolite extrudate catalyst. The reactor was then blanketed with nitrogen, heated to 225° C. and the reaction allowed to proceed for 6 hours at 225–250° C., at which time the norbornene was completely reacted. The reactor was then cooled to room temperature, the contents transferred to a distillation system and the excess tetralin removed by distillation. Analysis of the stripped product showed it to consist of 92.0 wt % norbornylated tetralin, 2.5 wt % residual tetralin and 5.5 wt % dinorbornylated tetralin. The product was a low-viscosity liquid at room temperature having a specific gravity (15.6° C.) of 1.0394, a pour point of −33° C. and a net heat of combustion of 151,022 BTU/gallon.

Example 3 - Preparation of Norbornylated Toluene 2518 gms of a 5:1 molar mixture of toluene:norbornene were charged to an agitated one-gallon stainless steel autoclave together with 150 gms of ZSM-5 zeolite extrudate catalyst. The reactor was then blanketed with nitrogen, heated to 150° C. and the reaction allowed to proceed for 19.8 hours at 150° C., at which time the norbornene was completely reacted. The reactor was then cooled to room temperature, the contents transferred to a distillation system and the excess toluene removed by distillation. Analysis of the stripped product showed it to consist of 82.7% mono-norbornylated toluenes, 7.5% di-norbornylated toluenes and 10.2 wt % norbornene oligomers (dimers and trimers). The mono-norbornylated fraction consisted of a mixture of ortho-, meta- and para-norbornylated toluenes. The product was a low viscosity liquid with a specific gravity of 0.990, a pour point of <−54° C., and a net heat of combustion of 145,154 BUT/gallon.

Example 4 - Preparation of Norbornylated $C_{12}$-Substituted Alkylbenzenes 1645 gms of a 3:1 molar mixture of $C_{12}$–$C_{14}$ substituted alkylbenzenes:norbornene were charged to an agitated one-gallon stainless steel autoclave together with 150 gms of ZSM-5 zeolite extrudate catalyst. The reactor was then blanketed with nitrogen, heated to 150° C. and the reaction allowed to proceed for 22.5 hours at 150° C., at which time the norbornene was essentially completely reacted. The reactor was then cooled to room temperature, the contents transferred to a distillation system and the norbornene dimer and norbornylated detergent alkylate recovered. Analysis showed the recovered mixture of norbornene dimer and norbornylated detergent alkylate to consist of 30.8 wt. % norbornene dimer and 64.4 wt. % norbornylated detergent alkylate. Analysis of the stripped product showed it to consist of 64.4 wt. % mono-norbornylated $C_{11}$–$C_{13}$ substituted alkylbenzenes, 7.5 wt. % di-norbornylated $C_{12}$-substituted alkylbenzenes and 30.8 wt. % norbornene dimer. The norbornylated alkylbenzenes (referred to as norbornylated detergent alkylate or NOA) are useful as a lubricant base stock and the norbornene dimer side product is useful as a high density fuel.

Changes and modifications in the specifically described embodiments can be carried out without departing from the scope of the invention which is intended to be limited only by the scope of the appended claims.

What is claimed is:

1. A process for the catalytic norbornylation of aromatics comprising contacting norbornene and an aromatic hydrocarbon with a solid catalyst comprising a porous crystalline material having a Constraint Index of from about 0.1 to about 12 under norbornylation conditions to evolve a product containing norbornylated aromatics and less than about 15 weight percent norbornene oligomers, wherein said porous crystalline material has the structure of at least one selected from the group consisting of ZSM-4, ZSM-5, ZSM-11, ZSM-22, ZSM-23, ZSM-35, ZSM-48, MCM-22, PSH-3, SSZ-25, and zeolite beta.

2. The process of claim 1 wherein said product contains less than about 10 weight percent of norbornene oligomers.

3. The process of claim 1 wherein said norbornylation conditions comprise temperature of from about 75 to about 300° C., pressure of from about 0 to about 1000 psig, and WHSV of from about 0.05 to about 10 hr.$^{-1}$.

4. The process of claim 3 wherein said norbornylation conditions further comprise temperature of from about 100 to 300° C., pressure from about 0 to about 750 psig, and WHSV of from about 0.05 to about 5 hr.$^{-1}$.

5. The process of claim 4 wherein said norbornylation conditions further comprise temperature of from about 125 to 275° C., pressure from about 0 to 500 psig, and WHSV of from about 0.1 to about 3 hr.$^{-1}$.

6. A process for selectively producing mono- and di-norbornylated aromatics comprising contacting norbornene and at least one aromatic hydrocarbon in aromatics:norbornene molar ratio of at least about 2:1 with a solid catalyst comprising a porous crystalline material having a Constraint Index of from about 0.1 to about 12 under norbornylation conditions to evolve a product containing mono- and di-norbornylated aromatics and less than about 15 weight percent norbornene oligomers, wherein said porous crystalline material has the structure of at least one selected from the group consisting of ZSM-4, ZSM-5, ZSM-11, ZSM-22, ZSM-23, ZSM-35, ZSM-48, MCM-22, PSH-3, SSZ-25, and zeolite beta.

7. The process of claim 6 wherein said product contains less than about 10 weight percent of norbornene oligomers.

8. The process of claim 6 wherein said norbornylation conditions comprise temperature of from about 75 to about 300° C., pressure of from about 0 to about 1000 psig and WHSV of from about 0.05 to about 10 hr.$^{-1}$.

9. The process of claim 8 wherein said norbornylation conditions further comprise temperature of from about 100 to 300° C., pressure from about 0 to about 750 psig, and WHSV of from about 0.05 to about 5 hr.$^{-1}$.

10. The process of claim 9 wherein said norbornylation conditions further comprise temperature of from about 125 to 275° C., pressure from about 0 to 500 psig, and WHSV of from about 0.1 to about 3 hr.$^{-1}$.

* * * * *